United States Patent
Ma

(10) Patent No.: US 10,138,186 B2
(45) Date of Patent: Nov. 27, 2018

(54) PROCESS FOR MAKING BIOBASED PROPYLENE GLYCOL FROM LACTIC ACID ESTERS

(71) Applicant: Archer Daniels Midland Company, Decatur, IL (US)

(72) Inventor: Chi Cheng Ma, Forsyth, IL (US)

(73) Assignee: Archer Daniels Midland Company, Decatur, IL (US)

( * ) Notice: Subject to any disclaimer, the term of this patent is extended or adjusted under 35 U.S.C. 154(b) by 0 days.

(21) Appl. No.: 15/517,128

(22) PCT Filed: Nov. 4, 2015

(86) PCT No.: PCT/US2015/058932
§ 371 (c)(1),
(2) Date: Apr. 5, 2017

(87) PCT Pub. No.: WO2016/081187
PCT Pub. Date: May 26, 2016

(65) Prior Publication Data
US 2017/0305821 A1    Oct. 26, 2017

Related U.S. Application Data

(60) Provisional application No. 62/081,333, filed on Nov. 18, 2014.

(51) Int. Cl.
C07C 29/149    (2006.01)
C07C 29/136    (2006.01)
C07C 31/20     (2006.01)

(52) U.S. Cl.
CPC ......... *C07C 29/149* (2013.01); *C07C 29/136* (2013.01); *C07C 31/20* (2013.01)

(58) Field of Classification Search
CPC ...... C07C 29/149; C07C 29/136; C07C 31/20
See application file for complete search history.

(56) References Cited

U.S. PATENT DOCUMENTS

| | | | | |
|---|---|---|---|---|
| 3,267,157 | A * | 8/1966 | Bunji Miya | C07C 51/36 502/20 |
| 4,283,581 | A * | 8/1981 | Wilkes | B01J 23/72 568/864 |
| 5,658,843 | A * | 8/1997 | Tsukada | B01J 23/60 502/344 |
| 7,615,671 | B2 * | 11/2009 | Puckette | C07C 29/149 568/862 |
| 2013/0281664 | A1 * | 10/2013 | Milstein | C07C 41/16 530/333 |

OTHER PUBLICATIONS

Adkins, H., et al., The hydrogenation of Esters to alcohols at 25-150 degrees, 1948, Journal of the American Chemical Society, vol. 7, No. 9, pp. 3121-3125 (Year: 1948).*

Maki-Arvela, P. et al., Production of Lactic acid/Lactates from biomass and their transformations to commodities, 2013, Chemical Reviews, vol. 114, pp. 1909-1971 (Year: 2013).*

* cited by examiner

*Primary Examiner* — Yate' K Cutliff
(74) *Attorney, Agent, or Firm* — William B. Miller

(57) ABSTRACT

A process is described for making a biobased propylene glycol product at least in part from a carbohydrate-derived feed, wherein a feed comprised of a lactic acid ester is reacted with hydrogen in the presence of a catalyst, in a nonaqueous solvent in which lactide may be essentially wholly solubilized at the conditions under which the reaction is carried out, so that lactide does not precipitate out to an extent whereby plugging of the reactor or fouling of the hydrogenation catalyst is observed.

6 Claims, No Drawings

PROCESS FOR MAKING BIOBASED PROPYLENE GLYCOL FROM LACTIC ACID ESTERS

CROSS-REFERENCE TO RELATED APPLICATION(S)

This application is a national stage entry of International Application No. PCT/US2015/058932, filed Nov. 4, 2015, which itself claims the benefit of U.S. Provisional Patent Application No. 62/081,333, filed Nov. 18, 2014, the contents of which are incorporated by this reference.

TECHNICAL FIELD

The present invention relates generally to processes for making biobased propylene glycol from renewable resources, and more particularly relates to processes for the hydrogenation of lactic acid and/or lactic acid esters to provide products including biobased propylene glycol.

Parenthetically, by "biobased", we mean those materials whose carbon content is shown by ASTM D6866 to be derived from or based in significant part (at least 20 percent or more) upon biological products or renewable agricultural materials (including but not being limited to plant, animal and marine materials) or forestry materials. "Wholly biobased" thus will be understood as referring to materials whose carbon content by ASTM D6866 is entirely or substantially entirely (for example, 95 percent or more) indicated as of biological origin.

In this respect ASTM Method D6866, similar to radiocarbon dating, compares how much of a decaying carbon isotope remains in a sample to how much would be in the same sample if it were made of entirely recently grown materials. The percentage is called the biobased content of the product. Samples are combusted in a quartz sample tube and the gaseous combustion products are transferred to a borosilicate break seal tube. In one method, liquid scintillation is used to count the relative amounts of carbon isotopes in the carbon dioxide in the gaseous combustion products. In a second method, 13C/12C and 14C/12C isotope ratios are counted (14C) and measured (13C/12C) using accelerator mass spectrometry. Zero percent 14C indicates the entire lack of 14C atoms in a material, thus indicating a fossil (for example, petroleum based) carbon source. One hundred percent 14C, after correction for the post-1950 bomb injection of 14C into the atmosphere, indicates a modern carbon source. ASTM D6866 effectively distinguishes between biobased materials and petroleum derived materials in part because isotopic fractionation due to physiological processes, such as, for example, carbon dioxide transport within plants during photosynthesis, leads to specific isotopic ratios in natural or biobased compounds. By contrast, the 13C/12C carbon isotopic ratio of petroleum and petroleum derived products is different from the isotopic ratios in natural or bioderived compounds due to different chemical processes and isotopic fractionation during the generation of petroleum. In addition, radioactive decay of the unstable 14C carbon radioisotope leads to different isotope ratios in biobased products compared to petroleum products.

BACKGROUND ART

Dihydroxyalkanes such as ethylene glycol and 1,2-propanediol (propylene glycol) have uses in a wide variety of applications, including as monomers in polyester resins, in antifreeze and deicing fluids, in the manufacture of food, drug and cosmetic products, and in liquid detergents.

Propylene glycol is predominantly currently produced by oxygenating propylene to produce the epoxide, propylene oxide. Propylene oxide is then typically reacted with water to form the desired 1,2-propanediol. Because the process begins with propylene, the cost to make propylene glycol has historically been linked to the price of oil and other hydrocarbon non-renewable resources.

Accordingly, in recent years significant resources have been devoted to the development of processes to make biobased propylene glycol from renewable resources, and biobased propylene glycol is now commercially produced by the hydrogenolysis of glycerol. A process for the manufacture of biobased propylene glycol by the hydrogenolysis of glycerol is described, for example, in U.S. Pat. No. 6,841,085 to Werpy et al., wherein compositions containing a 6-carbon sugar, sugar alcohol or glycerol are reacted with hydrogen over a Re-containing catalyst.

Glycerol is produced commercially as a byproduct of the biodiesel process, but requires costly purification to be useful as a feed to such a catalytic process for producing biobased propylene glycol. As well, biodiesel production is to a large degree dependent upon regulatory requirements and governmental incentives, so that carbohydrate-based routes to a biobased propylene glycol have also been proposed.

For example, U.S. Pat. No. 6,479,713 also to Werpy et al. (2002) proposes a process for the synthesis of propylene glycol by reacting hydrogen with a 5-carbon sugar, sugar alcohol, or lactic acid over the same Re-containing multimetallic catalyst. The hydrogenation of lactic acid is described as preferably being conducted in a temperature range of 110 to 200 degrees Celsius, and more preferably in the range of 140 to 170 degrees Celsius, under neutral to acidic conditions. Examples are provided wherein a solution of about 20 weight percent of lactic acid in deionized water is reacted with hydrogen at 2500 psi and at 150 degrees Celsius.

WO 2000/030744 (also published as U.S. Pat. No. 6,403,844 to Zhang et al), U.S. Pat. No. 6,455,742 to Cortright et al. (2002) in addition to the above-mentioned U.S. Pat. No. 6,479,713 to Werpy et al. (2002) that hydroxycarboxylic acids obtainable by fermentation of crude biomass, for example, lactic acid, have for some time also been viewed by the art as promising for glycols production.

More particularly, Simakova reports that a liquid phase hydrogenation of the carboxyl groups in such acids had been recognized as requiring a high hydrogen pressure and high catalyst loadings, so that various patents and articles had proposed the more facile reduction of hydroxycarboxylic acid esters. Still, according to Simakova, the reduction of hydroxycarboxylic acid esters in the liquid phase necessitated the use of high hydrogen pressures, referencing for example the work of Adkins et al. wherein hydrogen pressures from 20 to 30 MPa were used (see, e.g., Adkins and Billica, J. Am. Chem. Soc., vol. 70, pg 3118 (1948)), so that Simakova proposed a gas phase process wherein a mixture of esters of hydroxycarboxylic acid and hydrogen were reacted in the gas phase in the presence of a catalyst containing a "mixture of copper and/or oxide of copper and/or hydroxide of copper and/or salt or mixture of salts of copper and of inorganic acids of the element IVb, Va and VIa groups of periodic system, and oxide or mixture of oxides of the element IVb, Va and VIa groups of periodic system".

U.S. Pat. No. 6,455,742 to Cortright et al. proposes a process for catalytically reducing the carboxylic acid group of hydroxycarboxylic acids to a hydroxyl group, using hydrogen pressures of less than 50 atmospheres and a zero valent copper catalyst. The catalyst may be supported on silica, and hydroxyl groups on the silica may be capped with hydrophobic groups and silanes, such as trialkylsilanes. A vapor phase process is contemplated in one embodiment, while in other embodiments the lactic acid contacts the catalyst and hydrogen in the presence of water.

The last patent publication referenced by Simakova, namely, U.S. Pat. No. 6,403,844 to Zhang et al., provides a process for the production of propylene glycol in an aqueous reaction mixture of lactic acid and hydrogen with "an essentially pure ruthenium catalyst on an inert support at elevated pressure and temperature". Zhang et al. indicate that an important aspect of their invention is the capacity to convert unrefined or crude lactic acid in the form of a bacterial fermentate or in the form of lactic acid containing lactate salts (e.g., alkali metal, alkaline earth metal or ammonium salts of lactic acid) to propylene glycol, whereas the conversion processes of the prior art are described as requiring pure preparations of lactic acid or its esters.

Finally, Luo et al., "Effect of promoters on the structures and properties of the RuB/γ-$Al_2O_3$ catalyst", Journal of Molecular Catalysis A: Chemical, vol. 230, pp. 69-77 (2005) is similarly directed, in reviewing the effect of various promoters (Co, Fe, Sn, Zn) on the performance of a monometallic ruthenium/boron on alumina catalyst in the liquid phase hydrogenation of ethyl lactate to propylene glycol.

SUMMARY OF THE INVENTION

The present invention relates in one aspect to an improved process for obtaining a biobased propylene glycol product at least in part from a carbohydrate-derived renewable feed, wherein a feed comprised of a lactic acid ester is reacted in a liquid phase reaction in the presence of a catalyst with hydrogen from a hydrogen source, in a nonaqueous solvent in which lactide may be essentially wholly solubilized at the conditions under which the reaction is performed, so that lactide does not precipitate out to an extent whereby plugging of the reactor or fouling of the hydrogenation catalyst is observed.

In certain embodiments, lactide is completely solubilized at the conditions under which the reaction is performed and is not observed to precipitate out under reaction conditions.

In certain embodiments, a mixed feed comprised of glycerol and one or more lactic acid esters is used.

In certain embodiments, the nonaqueous solvent is propylene glycol.

In certain embodiments, the catalyst is a copper-containing catalyst.

In certain embodiments, the catalyst is a copper alloy-based sponge metal catalyst.

In certain embodiments, the catalyst is a Raney copper catalyst.

DESCRIPTION OF EMBODIMENTS

In a preferred embodiment, a process for obtaining a biobased propylene glycol product at least in part from a carbohydrate-derived renewable feed comprises reacting a lactic acid ester, such as may be obtained by the fermentation of dextrose to produce lactic acid and then the esterification of the lactic acid by reaction with an alcohol according to well-known and commercially practiced methods, in the liquid phase with hydrogen in the presence of a heterogeneous hydrogenation catalyst, using a nonaqueous solvent in which any lactide that is formed from the lactic acid under elevated temperature conditions may be solubilized, and not precipitate out to an extent whereby plugging of the reactor or fouling of the hydrogenation catalyst may be observed.

In one embodiment, the nonaqueous solvent is propylene glycol, especially a recycle portion of the biobased propylene glycol made by the process of the present invention. In another embodiment, the propylene glycol solvent forms substantially all of the liquid phase in which the process is conducted.

In an embodiment, the heterogeneous hydrogenation catalyst is a copper-containing catalyst. In other embodiments, the catalyst can be a copper alloy-based sponge metal catalyst, especially, a Raney copper catalyst prepared from an alloy comprising copper and aluminum and optionally further comprising a promoter such as zinc.

In a particular embodiment the catalyst selected is also useful, under the same reaction conditions as employed for the hydrogenation of the lactic acid ester, for the hydrogenolysis of glycerol to provide a biobased propylene glycol, so that a process for making a biobased propylene glycol product is contemplated from a combined feed including both a lactic acid ester and glycerol. The glycerol can comprise a greater or lesser part of such a combined feed in relation to the lactic acid ester portion of the combined feed, and the respective amounts of glycerol and lactic acid ester that can be used in the feed may be substantial both on an individual feed component basis and collectively, being practically limited only by solubility limits in the nonaqueous solvent.

A variety of lactic acid esters may be used, but those lactic acid esters that are highly soluble in propylene glycol under mild temperature conditions are particularly preferred, for example, propylene glycol lactate, ethyl lactate, propyl lactate and butyl lactate. As demonstrated by the examples which follow, such lactic acid esters may be fed to a fixed bed reactor in substantial concentrations in propylene glycol as a solvent, and readily react with hydrogen under mild temperature conditions and in the presence of a copper-containing catalyst (in the form of a Raney copper catalyst) to provide both a biobased propylene glycol product and to regenerate the alcohol from which the lactic acid ester had been formed originally (e.g., propylene glycol, ethanol, propanol or butanol) for recycle and reuse if desired.

Some propanol can additionally be expected by dehydration of propylene glycol, but the amount of propanol formed will be small, especially under the preferred mild temperature conditions, and the propanol will, with the ethanol, propanol or butanol from ethyl, propyl or butyl lactate feeds, respectively, be easy to separate by simple distillation from the propylene glycol product and solvent. Where propylene glycol lactate is employed as the feed for the process, of course, lactic acid can be combined with propylene glycol in a first step to form the propylene glycol lactate, and then additional propylene glycol can be added as appropriate to achieve a desired lactic acid ester feed concentration going into the second, lactic acid ester hydrogenation step. Propylene glycol is in any event formed by the hydrogenation step at high selectivity and with high conversion of the lactic acid esters, with no leaching observed from the catalyst.

Solutions of a lactic acid ester in propylene glycol which may be fed to the inventive process can be at least at a concentration of 10 percent by weight, but preferably will be at a concentration of at least 20 percent and more preferably will be at a concentration of at least 40 percent. Liquid hourly space velocities for the inventive process can be from 0.3 hr$^{-1}$, preferably from 0.5 hr$^{-1}$, and more preferably can be from 1.0 hr$^{-1}$ up to 3.0 hr$^{-1}$.

While the use of lactic acid esters as a starting material rather than lactic acid and while the use of a nonaqueous solvent in the substantial absence of water according to preferred embodiments will each have the benefit of reducing opportunities for corrosion within the reactor and also reduce opportunity for leaching of the catalyst, preferably mild temperature conditions and modest hydrogen pressures are employed for carrying out the hydrogenation. For example, reaction temperatures of not more than 250 degrees Celsius, preferably not more than 220 degrees Celsius and more preferably not more than 210 degrees Celsius can be employed with hydrogen pressures less than 17.2 MPa (2500 pounds per square inch), preferably less than 15.2 MPa (2200 pounds per square inch) and more preferably less than 14.5 MPa (2100 pounds per square inch).

The process of the present invention can be conducted in a batchwise, semi-batch or continuous manner, but preferably will be conducted continuously in a fluidized or especially a fixed bed reactor system.

The present invention is further demonstrated by the examples that follow:

EXAMPLES

Example 1

Lactide (417 g) purchased from NatureWorks LLC, Minnetonka, Minn. was combined with propylene glycol (1000 g), and the combination was heated to 125 degrees Celsius with stirring under low vacuum (300-500 torr) overnight, in a stirred batch reactor. The mixture was then cooled to room temperature to precipitate out any unreacted lactide. Conversion of the lactide was found to be greater than 96 percent, with the product mixture predominantly comprising propylene glycol dilactate, with smaller amounts of propylene glycol lactate, propylene glycol tetralactate and free lactic acid.

Example 2

A 180 cubic centimeter stainless steel, jacketed tubular reactor was loaded with a Raney copper catalyst. The reactor temperature was maintained by adjusting the temperature of the oil flowing through the jacket. An Isco dual piston pump and mass flow controllers were used to supply the lactate ester and hydrogen feeds to the reactor, with a condenser maintained at 0 degrees Celsius being used to collect the products from the reactor. Reactor pressure was controlled using a dome loaded back pressure regulator. A propylene glycol lactic acid ester feed prepared from lactide and propylene glycol in the manner of Example 1 was fed into the reactor as a 40 percent solution by weight in a propylene glycol solvent, at an LHSV of 0.5 hr$^{-1}$. Hydrogen was supplied concurrently in a hydrogen:ester feed ratio of 20:1 using 11.0 MPa (1600 psi) hydrogen, and reacted with the propylene glycol lactic acid ester feed at a reaction temperature of 210 degrees Celsius in the presence of the Raney copper catalyst. Conversion of the lactic acid esters was greater than 99 percent, with a selectivity to propylene glycol of greater than 96 percent. Propanol (in the form of 2-propanol) was produced as a minor byproduct, by the dehydration of propylene glycol.

Examples 3-13

The same 180 cubic centimeter reactor was used as in Example 2, to process a mixed feed comprised of equal parts of 20 percent each of refined glycerol and of the lactide-derived lactic acid ester feed used in Example 2, in the remainder of propylene glycol as a solvent. At 210 degrees Celsius, using 12.4 MPa (1800 psi) hydrogen and various liquid hourly space velocities, in the presence of a Raney copper catalyst the product mixtures were produced as shown below in Table 1, at the indicated product percent selectivities as determined by liquid chromatographic analysis. Propanol would be again obtained by the dehydration of propylene glycol, while minor amounts of ethylene glycol are also produced from the presumed hydrogenolysis of glycerol in the feed:

TABLE 1

| Example | LHSV | EG | PG | 2-propanol | 1-propanol | Lactic acid |
|---|---|---|---|---|---|---|
| 3 | 0.8 | 0.164 | 93.218 | 0.259 | 0.912 | 0 |
| 4 | 0.6 | 0.138 | 91.103 | 0.37 | 1.175 | 0 |
| 5 | 0.6 | 0.152 | 91.361 | 0.399 | 1.247 | 0 |
| 6 | 0.6 | 0.134 | 91.55 | 0.376 | 1.21 | 0 |
| 7 | 0.6 | 0.141 | 89.302 | 0.363 | 1.133 | 0 |
| 8 | 0.6 | 0.162 | 91.268 | 0.516 | 1.412 | 0 |
| 9 | 0.3 | 0.185 | 86.341 | 0.713 | 2.237 | 0 |
| 10 | 0.3 | 0.2 | 85.711 | 0.794 | 2.428 | 0 |
| 11 | 0.3 | 0.171 | 79.579 | 0.861 | 2.484 | 0 |
| 12 | 0.3 | 0.125 | 83.668 | 1 | 2.864 | 0 |
| 13 | 0.3 | 0.243 | 77.715 | 0.354 | 2.458 | 0 |

Example 14

An ethyl lactate ester feed was produced in the manner of Example 1, using ethanol rather than propylene glycol for the reactant with the lactide. A 40% solution of this ethyl lactate ester feed in propylene glycol was then converted as in previous examples, using 11.0 MPa (1600 psi) hydrogen, an LHSV of 1 hr$^{-1}$, a hydrogen:ester feed ratio of 20:1, a reaction temperature of 180 degrees Celsius and a Raney copper catalyst. Conversion of the lactic acid esters was again greater than 99 percent, with a selectivity to propylene glycol of 98.5 percent. Ethanol and propanol were produced as minor components.

Example 15

A butyl lactate ester feed was produced in the manner of Example 1, using butanol rather than propylene glycol for the reactant with the lactide. A 40% solution of this butyl lactate ester feed in propylene glycol was then converted as in previous examples, using 11.0 MPa (1600 psi) hydrogen, an LHSV of 1 hr$^{-1}$, a hydrogen:ester feed ratio of 20:1, a reaction temperature of 190 degrees Celsius and a Raney copper catalyst. Conversion of the lactic acid esters was again greater than 99 percent, with a selectivity to propylene glycol of 97 percent. Butanol and propanol were produced as minor components.

Example 16

A propyl lactate ester feed was produced in the manner of Example 1, using n-propanol (1-propanol) rather than propylene glycol for the reactant with the lactide. A 40% solution of this propyl lactate ester feed in propylene glycol was then converted as in previous examples, using 12.4 MPa (1800 psi) hydrogen, an LHSV of 1 hr$^{-1}$, a hydrogen:ester feed ratio of 20:1, a reaction temperature of 185 degrees Celsius and a Raney copper catalyst. Conversion of the lactic acid esters was again greater than 99 percent, with a selectivity to propylene glycol of 81.3 percent. Isopropyl and n-propyl alcohols were produced at 16.4 percent combined.

What is claimed is:

1. A process for making a biobased propylene glycol product at least in part from a carbohydrate-derived feed, comprising reacting a feed comprised of propylene glycol lactic acid ester with hydrogen in propylene glycol in the presence of a catalyst, in a liquid phase reaction.

2. A process according to claim 1, wherein the feed further comprises glycerol.

3. A process according to claim 2, further comprising recycling propylene glycol formed by the process, glycerol or both propylene glycol product and unconverted glycerol to the liquid phase in which the reaction is conducted.

4. A process according to claim 1, wherein the catalyst is a copper-containing catalyst.

5. A process according to claim 1, wherein the catalyst is a copper alloy-based sponge metal catalyst.

6. A process according to claim 5, wherein the catalyst is a Raney copper catalyst.

* * * * *